United States Patent
Tabary et al.

(10) Patent No.: US 10,386,508 B2
(45) Date of Patent: *Aug. 20, 2019

(54) METHOD OF CALIBRATING AN X RAY DIFFRACTION ANALYSIS SYSTEM

(71) Applicant: Commissariat a L'Energie Atomique et aux Energies Alternatives, Paris (FR)

(72) Inventors: Joachim Tabary, Grenoble (FR); Damien Barbes, Grenoble (FR); Caroline Paulus, Grenoble (FR)

(73) Assignee: Commissariat A L'Energie Atomique et aux Energies Alternatives, Paris (FR)

( * ) Notice: Subject to any disclaimer, the term of this patent is extended or adjusted under 35 U.S.C. 154(b) by 279 days.

This patent is subject to a terminal disclaimer.

(21) Appl. No.: 15/389,783

(22) Filed: Dec. 23, 2016

(65) Prior Publication Data

US 2017/0184739 A1    Jun. 29, 2017

(30) Foreign Application Priority Data

Dec. 24, 2015  (FR) ..................................... 15 63318

(51) Int. Cl.
*G01N 23/20091* (2018.01)
*G01T 7/00* (2006.01)
(Continued)

(52) U.S. Cl.
CPC ....... *G01T 7/005* (2013.01); *G01N 23/20091* (2013.01); *G01T 1/2907* (2013.01); *G01T 1/36* (2013.01); *G01N 2223/303* (2013.01)

(58) Field of Classification Search
CPC ......... G01N 23/2076; G01N 23/20025; G01N 23/20091; G01N 2223/316
(Continued)

(56) References Cited

U.S. PATENT DOCUMENTS

| | | |
|---|---|---|
| 2004/0109531 A1 | 6/2004 | Yokhin et al. |
| 2010/0124315 A1 | 5/2010 | Harding |
| 2017/0184518 A1* | 6/2017 | Barbes ............. G01N 23/20025 |

FOREIGN PATENT DOCUMENTS

WO   WO 2014/045045 A1   3/2014

OTHER PUBLICATIONS

French Preliminary Search Report (with Written Opinion) dated Sep. 23, 2016 in French Application 15 63318 filed on Dec. 24, 2015 (with English Translation of Categories of Cited Documents).

* cited by examiner

*Primary Examiner* — Courtney D Thomas
(74) *Attorney, Agent, or Firm* — Oblon, McClelland, Maier & Neustadt, L.L.P.

(57) ABSTRACT

The invention is a method of calibrating an X ray diffraction measuring system. The method includes moving a so-called calibration object along a propagation axis along which an irradiation beam propagates, the calibration object being adapted to occupy a plurality of successive positions along that axis. At each position of the object a spectrometry detector including at least one pixel acquires a spectrum of scattering radiation emitted by the object at an acute angle relative to the propagation axis. The method includes, in various spectra corresponding to various respective positions of the object, the identification of a so-called calibration peak and obtaining a parameter of said peak, which parameter can be the intensity or the energy of said peak. The parameters obtained on the various peaks then make it possible to establish an associated pixel dispersion function.

10 Claims, 9 Drawing Sheets

(51) Int. Cl.
*G01T 1/29* (2006.01)
*G01T 1/36* (2006.01)

(58) Field of Classification Search
USPC .................................................. 378/70–89
See application file for complete search history.

$I_{k,c,z}$ $$E = \frac{hc\chi}{sin\left(\frac{\theta_k}{2}\right)}$$

METHOD OF CALIBRATING AN X RAY DIFFRACTION ANALYSIS SYSTEM

TECHNICAL FIELD

The technical field of the invention is the analysis of an object by spectrometric analysis of ionizing radiation diffracted by said object. The invention applies equally well to analysis of biological tissues for diagnostic purposes and to non-destructive testing in the industrial field or for applications linked to security.

PRIOR ART

Energy Dispersive X Ray Diffraction (EDXRD) spectrometry is a nondestructive analysis technique used for the identification of materials constituting an object. This technique is based on the elastic scattering of an ionizing electromagnetic radiation, also termed Rayleigh scattering. It has already been applied in the detection of explosives or other elicit substances. Generally speaking, this technique consists in irradiating an object with poly-energetic X rays and determining the energy spectrum of radiation scattered by the object at low scattering angles, typically between 1° and 20° inclusive, relative to the trajectory of the X rays incident on the object. The analysis of this spectrum makes it possible to identify the materials constituting the object. In fact, most materials have a particular spectral signature, depending on their atomic or molecular structure. Comparison of the measured scattering spectra with signatures of known materials makes it possible to determine the composition of the object.

In devices known until now, a source of irradiation produces poly-energetic X rays propagating toward an object, a primary collimator or pre-collimator being disposed between the source and the object so as to form a finely collimated beam of X rays toward the object. A second collimator is then placed between the analyzed object and a detector adapted to acquire an energy spectrum of the radiation scattered by the object.

The volume of the analyzed object corresponds to an intersection between said beam, propagating through the object, and an observation field of the detector, that field being defined, among other things, by the aperture of the second collimator and the size of the detector. Accordingly, for the same detector, the observation field is proportional in size to the aperture of the second collimator. This makes it possible to increase the volume of the observed object and to increase the quantity of scattered radiation detected.

However, if the observation field is increased, the detector may detect photons scattered by different parts of the object with different scattering angles. Now, the scattering angle is a key parameter because it makes it possible to convert the measured data, taking the form of energy spectra, into spectral signatures representative of the material constituting the examined object, the latter generally being expressed in the form of a magnitude termed the momentum transfer. Moreover, the analyzed object may not be homogeneous and comprise different parts, each of these having its own spectral signature. It is therefore of interest to be able to divide the object spatially into different elementary volumes and to determine a spectral signature, termed the scattering signature, associated with each of these elementary volumes.

Because of this, an angular and/or spatial dispersion function of the measuring device must be determined during a calibration procedure. The inventors have established an experimental method making it possible to obtain a dispersion function of this kind.

STATEMENT OF THE INVENTION

One object of the invention is a method of calibrating a device for analyzing an object, said analysis device including:
  a source of irradiation adapted to irradiate said object, configured to emit ionizing electromagnetic radiation propagating toward the object along a propagation axis;
  a detector including at least one pixel and adapted to detect radiation scattered by the object irradiated in this way and to acquire an energy spectrum thereof, said scattered radiation propagating in a direction at an acute so-called scattering angle relative to said propagation axis;
the calibration method including the following steps:
  a) irradiating a calibration object by said irradiation source so that at least one pixel of said detector detects radiation scattered by the calibration object irradiated in this way and acquires an energy spectrum thereof;
  b) moving the calibration object to successive different positions along said propagation axis and, at each position of the object, acquisition, by said pixel of a spectrum of the radiation scattered by said calibration object, termed calibration spectrum, each calibration spectrum being associated with a position of the calibration object;
  c) in each calibration spectrum acquired during the step b), identification of a characteristic calibration peak of said calibration object;
  d) determining a parameter of each calibration peak identified in the step c);
  e) obtaining a dispersion function associated with said pixel from parameters determined during the step d) at the various positions of said calibration object, said dispersion function representing a dispersion of the intensity and/or the scattering angle of scattered radiation detected by said pixel at the various positions of the calibration object.

The term "peak parameter" means an intensity (or amplitude) of the peak, that is to say a parameter representing the area or the height of that peak, and/or an energy associated with that peak, that is to say a parameter representing the energy with which that peak is detected.

According to an embodiment,
  step d) includes determining an intensity of said calibration peak identified in each calibration spectrum; and
  step e) includes determining a so-called intensity spatial dispersion function from the intensities of the calibration peak determined at each position of the calibration object, said dispersion function representing a quantity of scattered radiation detected by said pixel as a function of the position of the calibration object.

According to an embodiment,
  step d) includes determining an energy of said calibration peak identified in each calibration spectrum; and
  step e) includes:
    calculating a scattering angle from said energy determined in each calibration spectrum; and
    determining a so-called spatial dispersion function of the scattering angles from the scattering angles obtained at each position of the calibration object, said dispersion function representing the scattering angles of the scattered radiation detected by said pixel as a function of the position of the calibration object.

In this embodiment, step f) may include determining a mean scattering angle for said pixel.

According to an embodiment:
step d) includes determining an intensity and the energy of said calibration peak identified in each calibration spectrum; and
step e) includes:
calculating a scattering angle from said energy determined at each calibration peak, said scattering angle being associated with said intensity of said calibration peak; and
determining a so-called intensity angular dispersion function representing a distribution of the intensity of the scattering radiation detected by said pixel as a function of the scattering angle of that radiation.

According to this embodiment, the method can include a step f') of interpolating the intensity angular dispersion function between the various scattering angles obtained in the step e) at each position of the calibration object so as to obtain a so-called interpolated intensity angular dispersion function. The method can also include a step g) of determining an angular response matrix associated with said pixel from said interpolated intensity angular dispersion function, wherein each row or column of said matrix are associated with an energy and representing a probability distribution of the momentum transfer when said pixel detects scattering radiation with said energy.

The calibration object is an object the composition of which is known.

According to one embodiment, the detector includes a plurality of pixels and the method includes a determination of said dispersion function for each pixel. The pixels can be virtual pixels produced by sub-pixelization of physical pixels of the detector.

Another object of the invention is an information storage medium readable by a processor including instructions for the execution of the steps c) to e) of the calibration method described above using acquisition spectra acquired by a pixel of a detector, the spectrum being acquired according to the steps a) and b) of the calibration method described above, those instructions being executable by the processor.

FIGURES

FIG. 3D represents the spectrum from FIG. 3C after normalization of the latter by a so-called transmission spectrum.

Figure 4A:
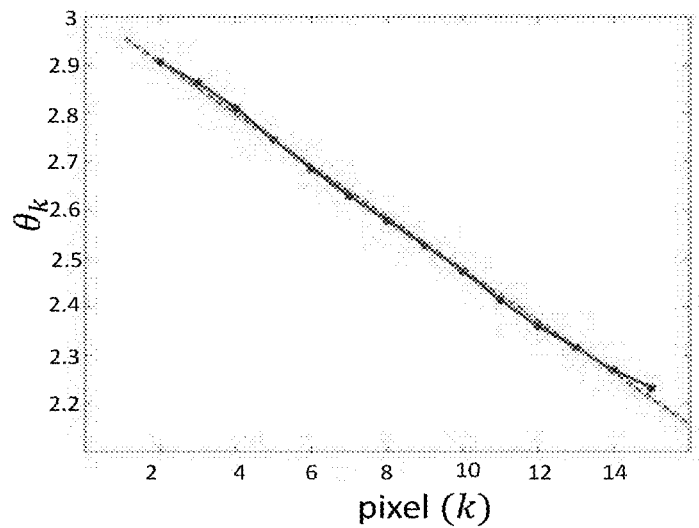
FIG. 4A is a curve plotting a mean scattering angle associated with various pixels, on which is plotted in dashed line a linear trend curve.
Figure 4B:
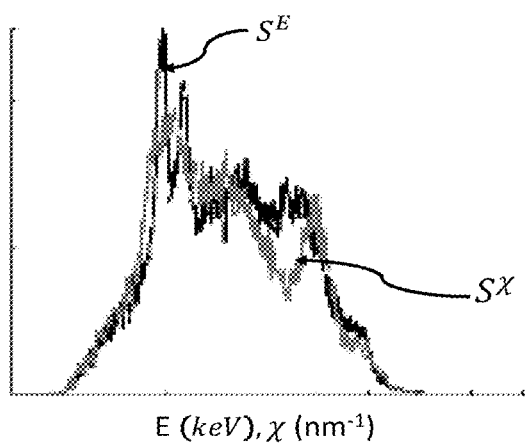

FIG. 4B represents an energy spectrum obtained by summing energy spectra respectively acquired by different pixels, as well as a momentum transfer spectrum obtained by summing momentum transfer spectra obtained by said pixels, each momentum transfer spectrum of a pixel being obtained by applying a change of variable to the energy spectrum acquired by said pixel, said change of variable taking account of the mean scattering angle associated with said pixel.

Figure 5A:
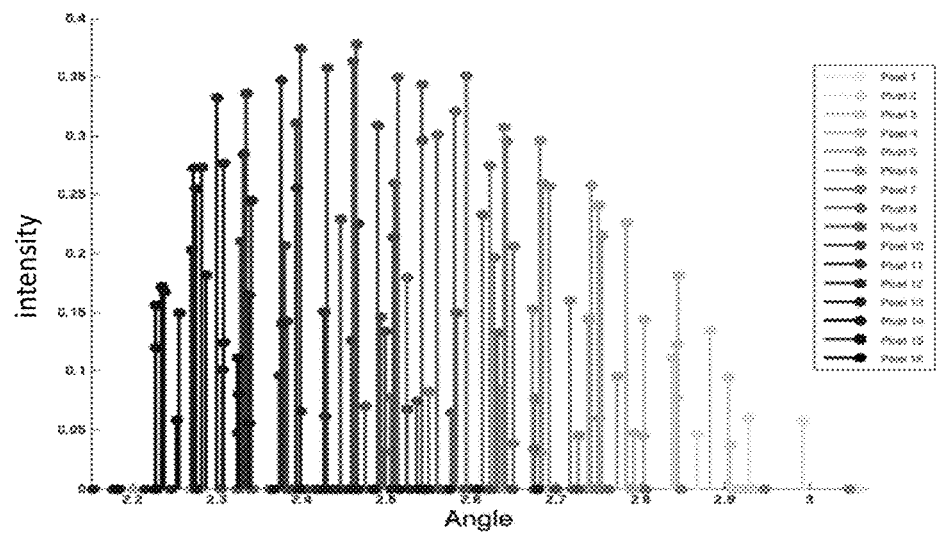

FIG. 5A represents a so-called intensity angular dispersion function established for a plurality of pixels.

Figure 5B:
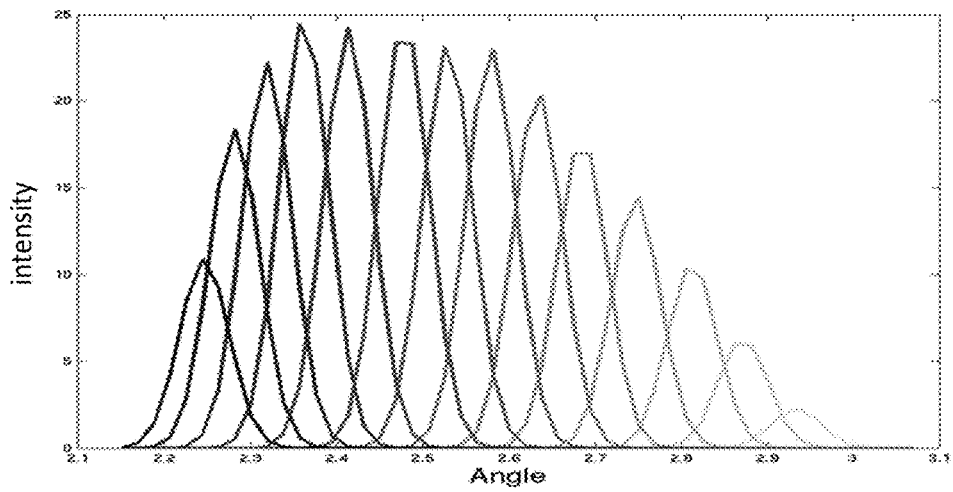

FIG. 5B shows an interpolated intensity angular dispersion established for the pixels referred to in connection with FIG. 5A.

Figure 5C:
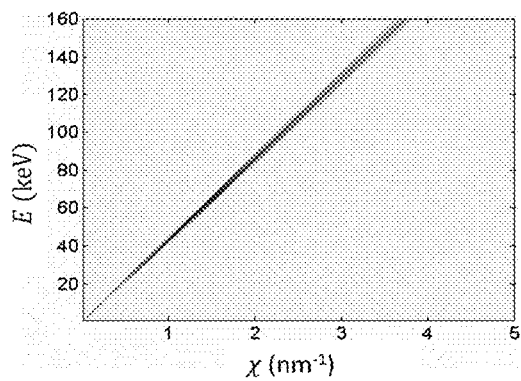

FIG. 5C is an illustration of a so-called angular dispersion matrix associated with a pixel.

Figure 5D:
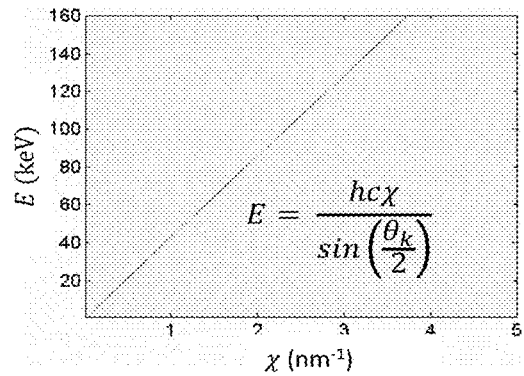

FIG. 5D is an illustration of another angular dispersion matrix associated with that pixel.

Figure 6A:
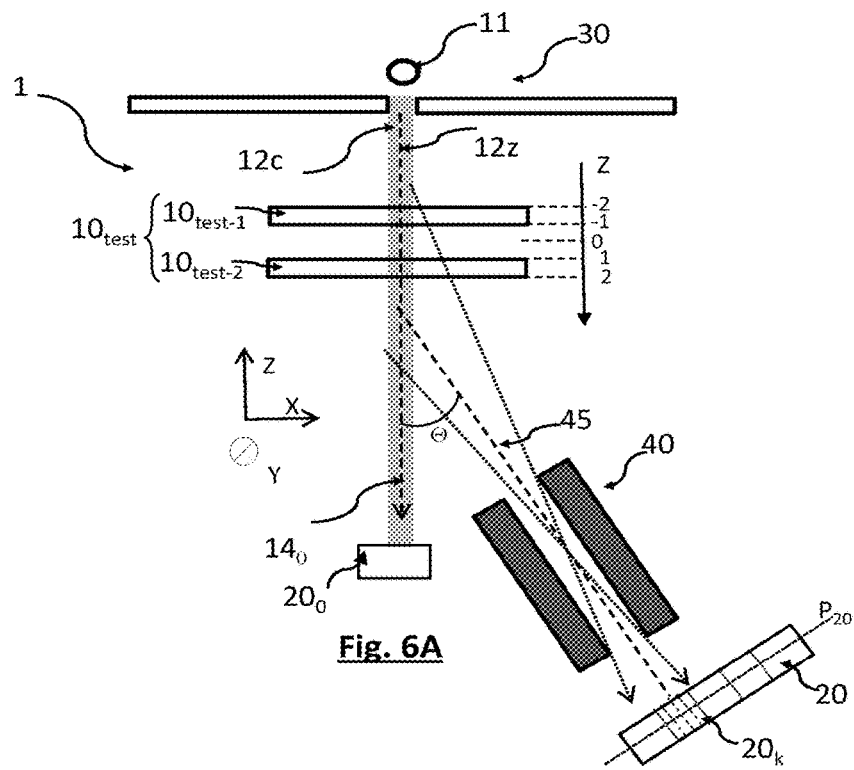

FIG. 6A represents an experimental device using a test object.

Figure 6B:
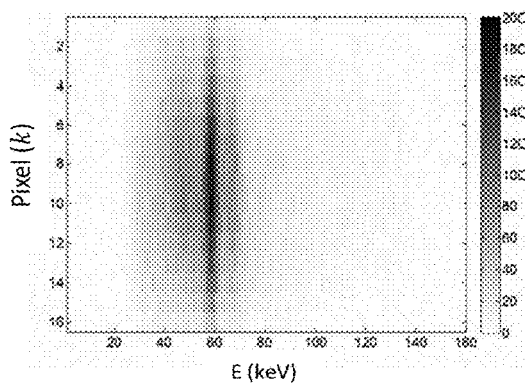

FIG. 6B shows various scattering spectra acquired by virtual pixels obtained using a reference material, in this instance PMMA (Poly(methyl methacrylate)).

Figure 6C:
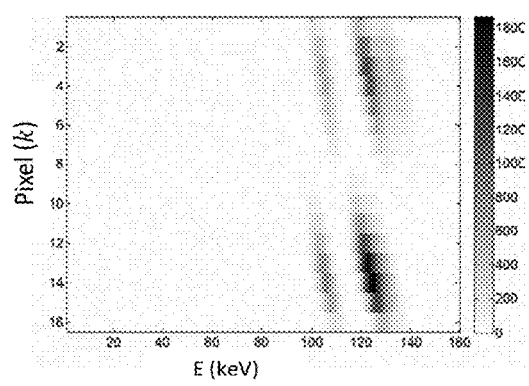

FIG. 6C shows various scattering spectra acquired by various virtual pixels during an experimental test using a test object.

Figure 6D:
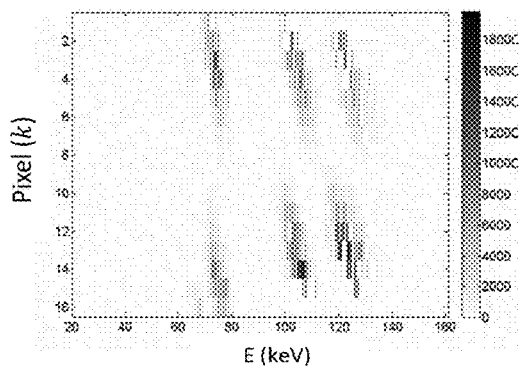
Figure 6E:
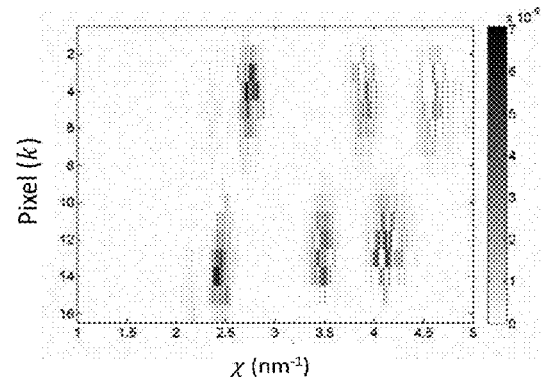

FIGS. 6D and 6E represent response functions measured by various pixels, respectively expressed as a function of energy or as a function of momentum transfer.

Figure 6F:
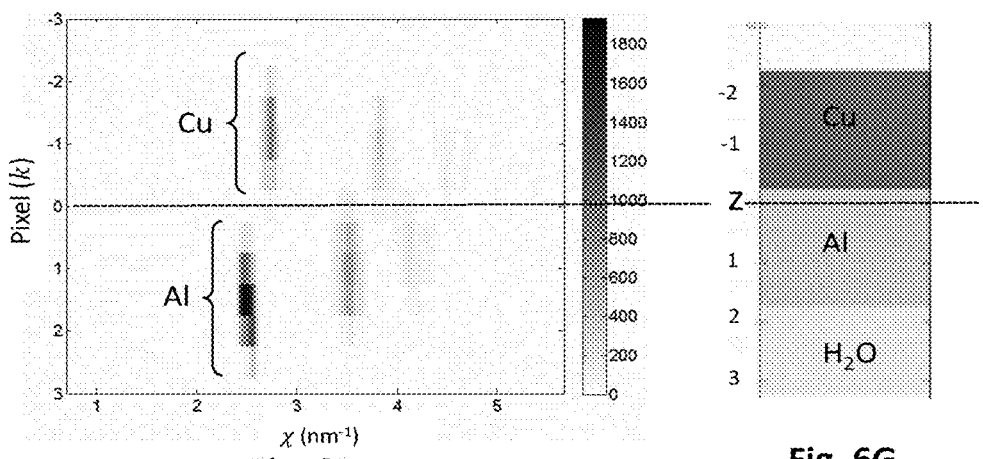

FIG. 6F represents the spectral signatures of various elementary volumes obtained from the response functions shown in FIG. 6E.

Figure 6G:
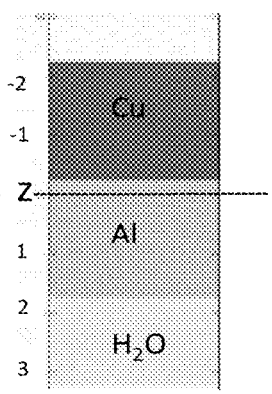

FIG. 6G illustrates the various materials identified in the test object.

DESCRIPTION OF PARTICULAR EMBODIMENTS

Figure 1A:
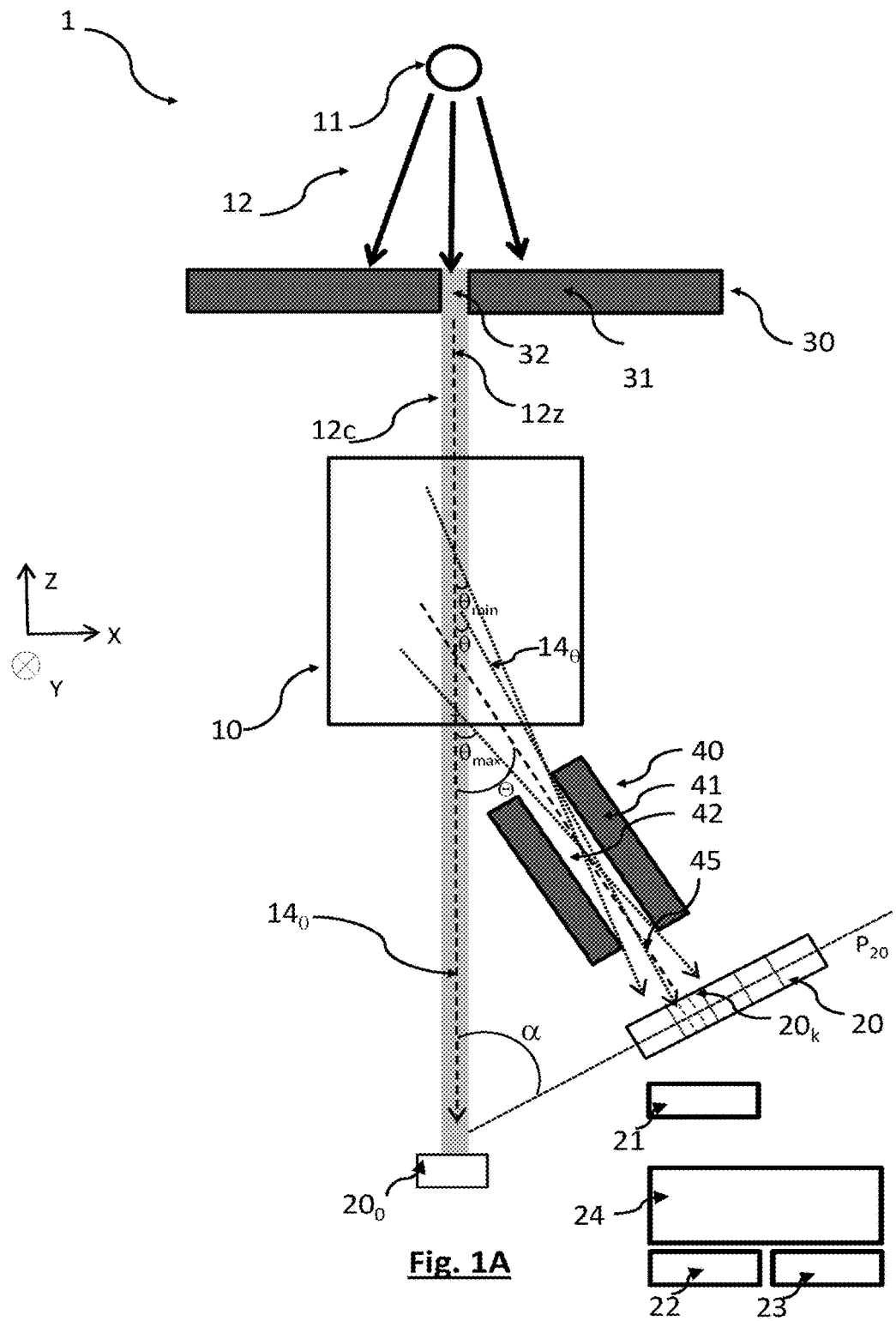
FIG. 1A represents one example of a device according to the invention for analyzing an object by X ray diffraction.

FIG. 1A represents an exemplary device 1 for analyzing an object 10 by X ray diffraction spectrometry. An irradiation source 11 emits ionizing electromagnetic radiation 12 propagating towards the object 10 the composition of which it is required to determine.

The device includes a first collimator or pre-collimator 30 adapted to collimate the radiation emitted by the irradiation source 11 to form an incident collimated beam $12_c$ propagating towards the object along a propagation axis $12_z$. The device also includes a detector 20 including pixels $20_k$, each pixel being adapted to detect radiation $14_\square$ scattered by the object 10 in a direction at a scattering angle θ relative to the propagation axis $12_z$. This radiation results for example from elastic scattering of radiation forming the incident collimated beam $12c$.

The analysis device 1 includes a second collimator 40 disposed between the object 10 and the detector 20. The second collimator 40 makes it possible to direct selectively scattering radiation $14_θ$ scattered by the object 10 at a scattering angle θ relative to the propagation axis $12_z$ in an angular range Δθ. By directing selectively is meant that radiation scattered at an angle not included in this angular range Δθ is attenuated by the second collimator.

The analysis device 1 is placed in a frame of reference to which is tied an orthogonal frame of reference X, Y, Z as represented in FIG. 1A.

The term ionizing electromagnetic radiation designates electromagnetic radiation consisting of photons with an energy greater than 1 keV and preferably less than 5 MeV. The energy range of the ionizing radiation may be between 1 keV and 2 MeV inclusive, but most often lies between 1 keV and 150 keV or 300 keV. The ionizing radiation may be X radiation or γ radiation The ionizing radiation source is preferably poly-energetic, the incident radiation being emitted in an energy range generally extending over several tens or even hundreds of keV. It is notably a tube emitting X rays.

The irradiation source 11 is an X ray tube with a tungsten anode at a voltage, generally between 40 and 170 kV inclusive, that can be varied in order to modify the energy range of the incident radiation 12. The detector includes pixels distributed along a line or in a two-dimensional matrix, each pixel extending over an area of 2.5*2.5 mm², its thickness being 5 mm. The material constituting each pixel is a semiconductor, for example CdTe or CdZnTe or any other material adapted to produce spectrometric measurements, preferably at room temperature. It could equally be a scintillator type material, with sufficient energy resolution. The detector is energy resolved and each pixel makes it possible to obtain spectra with energy channels of the order of 1 keV. The irradiation source 11 may include a screen made of metal, for example copper, to block the propagation toward the pre-collimator 30 of radiation with an energy less than 20 keV. When this screen is made of copper, its thickness is equal to 0.2 mm, for example.

The first collimator or pre-collimator 30 includes a block of dense material 31, including tungsten, for example, adapted to absorb virtually all of the radiation 12 emitted by the irradiation source 11. It includes a narrow opening 32 extending along a so-called propagation axis $12_z$ allowing the passage of a narrow collimated beam $12_c$. By narrow opening is meant an opening the diameter or the largest diagonal of which is less than 2 cm, or even less than 1 cm. In this example, the opening is a cylinder of 1 mm diameter.

The object 10 may be an industrial component the quality or the composition of which it is wished to determine. It may equally well be luggage to be checked. The device 1 is then used for nondestructive testing purposes. It may equally be living biological tissue, for example a part of the body of an animal or of a human being. The device is then a medical analysis device used to assist diagnosis. The body part may in particular be an organ in which, following a first examination, for example an X ray or a scan, the presence of an anomaly is suspected, in particular a cancerous tumour.

The second collimator 40 includes walls 41 made from a dense material adapted to absorb virtually all of the radiation $14_θ$ scattered by the object outside the angular range previously referred to. An opening in said dense material defines a channel 42 extending along a median axis 45. By median axis is meant an axis extending along the channel equidistantly from the walls delimiting the channel. This median axis 45 is inclined relative to the propagation axis $12_z$ of the incident collimated beam $12_c$. The angle Θ between the median axis 45 of the channel 42 and the propagation axis $12_z$, termed the collimation angle, is strictly greater than 0° and less than 20°. The collimator is then able to transmit toward the detector 20 scattered radiation $14_θ$ propagating at an angle, termed the scattering angle, θ, in a defined angular range Δθ around the collimation angle Θ. FIG. 1A shows two scattered rays $14_θ$ delimiting the observation field Δθ of the second collimator 40, their respective scattering angles constituting the limits $θ_{min}$ and $θ_{max}$ of the angular range associated with the second collimator 40. The length of each channel is typically between 50 and 100 mm inclusive, while the opening extends a few hundred microns, for example 500 μm, in a direction perpendicular to the median axis.

In the embodiment represented in FIG. 1A, the second collimator 40 includes only one channel 42. In other embodiments the collimator 40 may include a plurality of channels $42_n$ disposed for example parallel to one another, each channel being associated with a collimation angle $Θ_n$ and an angular range $Δθ_n$.

The radiation detector is a detector comprising pixels $20_k$ arranged in a plane $P_{20}$ termed the detection plane. The index k designates a coordinate of each pixel in the detection plane $P_{20}$. The pixels may extend along a line but generally extend in a two-dimensional regular matrix. In the example described in this application, the detection plane $P_{20}$ extends in a direction at an angle a strictly less than 90° relative to the propagation axis $12_z$ of the collimated incident radiation $12_c$. This angle α is preferably between 70° and 88° or 89°. The detection plane $P_{20}$ is preferably orthogonal to the median axis 45 of the channel 42 of the second collimator 40.

Each pixel $20_k$ constituting the radiation detector 20 includes:
- a detector material adapted to interact with the photons of scattered radiation $14_θ$ transmitted by the object 10 via the second collimator 40, this material being of scintillator type or preferably a semiconductor material compatible with use at room temperature, of CdTe or CdZnTe type;
- an electronic circuit 21 adapted to generate a signal the amplitude A of which depends on and is preferably proportional to an energy E deposited by each photon interacting in the detector material;
- a spectrometry circuit adapted to establish an energy spectrum $S_k^E$ of the signals detected during a time period determined the acquisition period.

Each pixel $20_k$ is therefore adapted to produce a spectrum $S_k^E$ of the radiation $14_θ$ scattered by the object.

The term energy spectrum designates a histogram of the amplitude A of the signals detected during a period of acquisition of the spectrum. A relation between the amplitude A of a signal and the radiation energy E can be obtained by means an energy calibration function g such as E=g(A), according to principles known to the person skilled in the art. An energy spectrum $S_k^E$, can therefore take the form of a vector, each term $S_k^E(E)$ of which represents a quantity of radiation detected by the pixel $20_k$ in an energy range $$E \pm \frac{\partial E}{2},$$

where ∂E is the spectral width of an energy discretization increment of the spectrum.

The device also includes a calculation unit or processor 22, for example a microprocessor, adapted to process each spectrum $S_k^E$ acquired by the pixels $20_k$ of the detector 20. In particular, the processor is a microprocessor connected to a programmable memory 23 in which is stored a sequence of instructions for effecting the spectrum processing and calculation operations described in the present description. These instructions may be saved on a storage medium that can be read by the processor, of the hard disk, CDROM or other memory type. The processor may be connected to a display unit 24, for example a screen.

Each pixel $20_k$ is connected to an electronic circuit 21 for collecting signals representative of the energy of scattering radiation transmitted by the collimator 40. The detector 20 may be connected to the processor 22 described above, making possible a first stage of processing consisting in analyzing the signals emitted by a plurality of adjacent pixels so as to locate the point of impact of the detected radiation with a spatial resolution less than the increment at which these pixels are distributed. This kind of processing, known to the person skilled in the art as sub-pixelization or super-pixelization, amounts to forming so-called virtual pixels $20'_k$, the area of each virtual pixel being less than 1 mm * 1 mm or even 0.5 mm by 0.5 mm, for example. In the present example, the size of the virtual pixels is 150 μm by 150 μm. This increases the spatial resolution of the detector 20. This kind of decomposition of the virtual pixels is known to the person skilled in the art. It has already been described in Warburton W. K., "An approach to sub-pixel spatial resolution in room temperature X-ray detector arrays with good energy resolution" and Montemont et al. "Studying spatial resolution of CZT detectors using sub-pixel positioning for SPECT", IEEE transactions on nuclear science, Vol. 61, N°5, October 2014.

In the remainder of the text, references to pixels $20_k$ may refer interchangeably to physical or virtual pixels. This preferably means virtual pixels because of the improved spatial resolution of the detector this achieves.

The device 1 preferably includes a so-called auxiliary detector $20_0$ in a so-called transmission configuration adapted to detect not radiation scattered by the object retained on the support but instead radiation $14_0$ transmitted by the object 10 in the direction $12_z$ of the incident beam $12_c$. This so-called transmission radiation is transmitted by the object 10 without having interacted with it. The auxiliary detector $20_0$ makes it possible to establish a spectrum $S_0^E$ of the radiation $14_0$ transmitted by the object 10 along the propagation axis $12_z$ of the incident collimated beam $12_c$. This kind of spectrum can be used to determine an attenuation spectral function Att of the object, as described later.

Figure 1B:
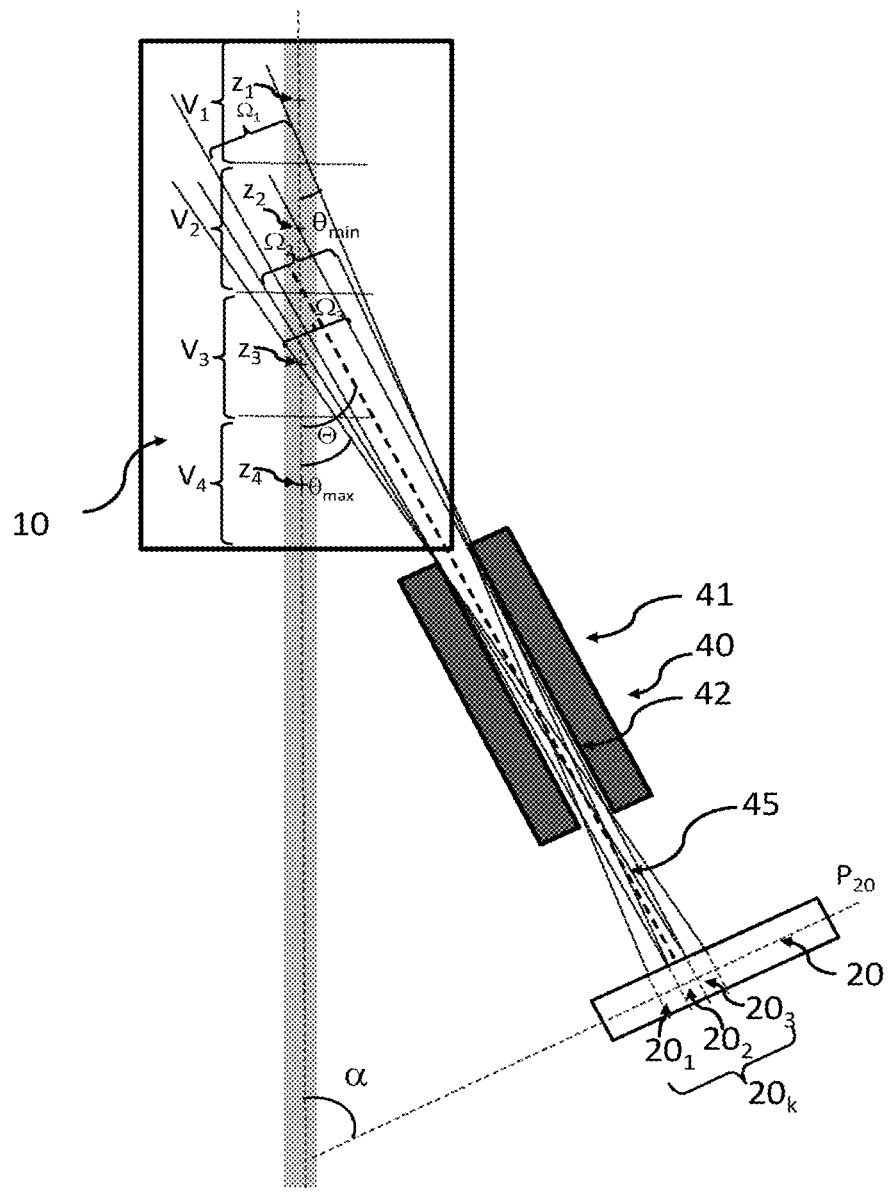
FIG. 1B represents a detailed view of FIG. 1A, showing the observation field of each pixel and the decomposition of the object into elementary volumes.

FIG. 1B represents in more detail the object 10 and the observation field produced by the collimator 40. There can be seen in this figure three pixels $20_1 \ldots 20_3$ adapted to receive scattering radiation $14_\theta$, each pixel being associated with an observation field $\Omega_1, \Omega_2, \Omega_3$. The observation field of each pixel is defined by the size of said pixel and by the geometry of the collimator 40. The object can moreover be sampled according to a plurality of elementary volumes $V_1 \ldots V_{NZ}$, regularly or otherwise, each elementary volume $V_z$ being associated with a coordinate z along the propagation axis $12_z$ of the incident collimated beam $12_c$. $N_z$ is the number of elementary volumes $V_z$ concerned. There are represented in FIG. 1B four elementary volumes $V_1, V_2, V_3$ and $V_4$, centred on respective coordinates $z_1, z_2, z_3$ and $z_4$ along the propagation axis. The basic idea of the invention is to obtain an angular dispersion function and a spatial dispersion function characterizing this device. These dispersion functions make it possible to estimate the composition of each elementary volume from the spectra $S_k^E$ acquired by the various pixels $20_k$ of the detector 20. Because of the aperture of the collimator, the same elementary volume $V_z$ can emit scattered radiation toward different pixels $20_k$ of the detector, especially if the detector is divided into virtual pixels of small size. The spectrum $S_k^E$ measured by each pixel results from the detection of scattered radiation $14_\theta$ with different scattering angles θ by different elementary volumes $V_z$ of the object 10. Sampling elementary volumes independent of the observation field of each pixel makes it possible to reconstruct the object according to a fine sampling, determined arbitrarily.

During the analysis, the object 10 is irradiated by the incident poly-energetic beam $12_c$.

Because of the effect of the Rayleigh scattering, a portion of the incident radiation $12_c$ is scattered in a plurality of directions, the scattering radiation intensity being higher or lower according to the combination of the energy of the photons and the scattering direction. This variation of intensity as a function of the scattering angle θ form a scattering signature specific to each material. In the case of a crystal, the scattering intensity is non-zero only in precise incident photon energy/scattering angle pair configurations defined by the Bragg equation:

$$2d\sin\left(\frac{\theta}{2}\right) = n\frac{hc}{E} \qquad (1)$$

where:
d is a characteristic distance of the atomic or molecular arrangement of a material constituting the irradiated object. If the material analyzed is a crystal, d corresponds to the inter-reticular distance;
n is an integer designating the order of the interference;
E is the the energy of the scattered radiation, expressed in keV;
θ is the scattering angle;
h and c respectively designate Planck's constant and the speed of light.

It is common to express a magnitude designated by the term momentum transfer and represented by the letter χ, expressed in $nm^{-1}$, as follows:

$$\chi = \frac{\sin\left(\frac{\theta}{2}\right)E}{hc} \qquad (2)$$

To each pixel or virtual pixel $20_k$ of the detector 20 there corresponds a so-called mean scattering angle $\theta_k$ representing the most probable angle at which scattering radiation $14_\theta$ detected by the pixel propagates. The benefit of super-pixelization is to end up with small pixels, which reduces the angular range of the scattering radiation likely to reach one of them.

Figure 2:
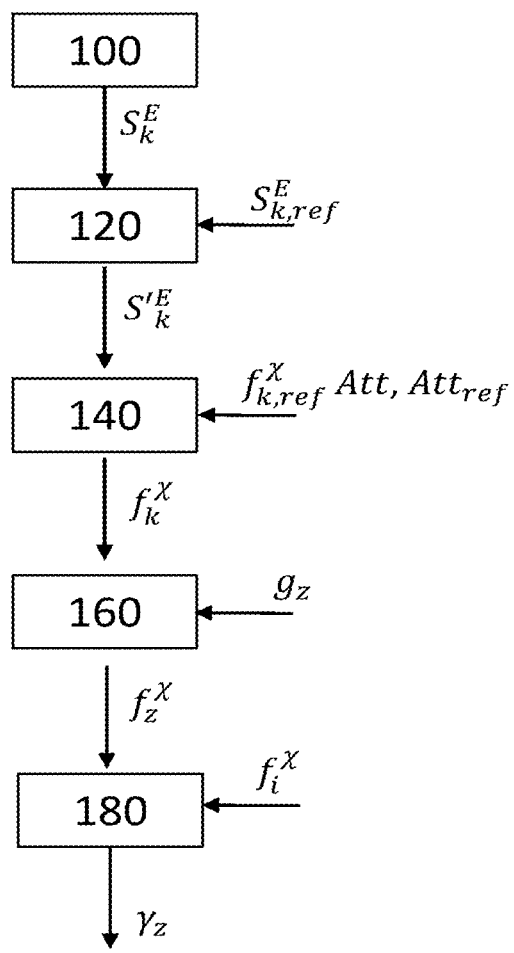
FIG. 2 represents the main steps of a method of analyzing an object using the device represented in FIGS. 1A and 1B.

The main steps of the analysis of an object are described next with reference to FIG. 2.

During a first step 100, the object 10 is irradiated by the irradiation source 11 and each pixel $20_k$ of the detector 20 acquires a spectrum $S_k^E$ of the scattering radiation $14_\theta$ to which it is exposed. In this example, the collimation angle Θ may be between 1° and 20° inclusive. The exponent E represents the fact that here the spectrum is a function of energy. Knowing the scattering angle $\theta_k$ associated with each pixel $20_k$, it is possible to express a scattering spectrum not as a function of energy but as a function of the momentum transfer χ by proceeding to a change of variable according to equation (2), in which case the spectrum is designated $S_k^\chi$.

The energy spectrum may be expressed according to the following equation:

$$S_k^E = D_{k'}(S_{inc} \times Att \times (A_k f_k^\chi)) \qquad (3)$$

where:
- $S_k^E$ is the energy spectrum measured by the pixel $20_k$, of dimension $(N_E, 1)$; $N_E$ is the number of channels of the spectrum, i.e. the number of energy discretization increments;
- $D_k$ is a response matrix of the pixel $20_k$ representing the detection imperfections. Each term $D_k(E, E_i)$ of this matrix represents a probability that a photon of energy $E_i$ incident on the detector will be considered by the detector as having an energy E. Here this matrix is a square matrix of size $N_E * N_E$;
- $S_{inc}$ is an energy spectrum of the incident collimated beam $12_c$, of dimension $(N_E, 1)$;
- Att is a vector, termed the attenuation spectral function, representing an attenuation of the incident spectrum by the object 10, of dimension $(N_E, 1)$;
- $A_k$ is an angular dispersion matrix associated with each pixel $20_k$, of size $(N_E, N_\chi)$, where
- $N_\chi$ represents the number of discretization increments of the momentum transfer $\chi$. Each term $A_k(E,\chi)$ represents a probability that the energy of a photon of energy E detected by a pixel $20_k$ corresponds to a momentum transfer equal to $\chi$, in the light of equation (2). Applying this matrix makes it possible to effect a change of variable between a spectrum $S_k^E$ measured by said pixel and expressed as a function of the energy E and this same spectrum $S_k^\chi$ expressed as a function of the momentum transfer transfer $\chi$. The establishing of this matrix will be described in detail later, in relation to the determination of an angular dispersion function of the scattering intensities associated with the pixel. In a first approach, the angular response matrix $A_k$ may be considered as being the matrix representing a one-to-one function representing a change of variable with $A_k(E, \chi) = 1$ if $$E = \frac{hc\chi}{\sin\left(\frac{\theta_k}{2}\right)},$$

where $\theta_k$ represents a mean scattering angle associated with the pixel $20_k$ concerned. The determination of this mean scattering angle $\theta_k$ will be explained hereinafter;
- $f_k^\chi$ is a scattering function associated with each pixel $20_k$. This is a spectrum of values of the momentum transfer $\chi$ measured by said pixel $20_k$. This scattering function depends only on materials present in the elementary volumes $V_z$ lying in the observation field $\Omega_k$ of said $20_k$. The dimension of $f_k^\chi$ is $(N_\chi, 1)$;
- × is the Hadamard product (term by term product) and · is the matrix product.

Moreover, in this example, it is considered that the energy resolution of the detector is good enough for the response matrix $D_k$ of each pixel $20_k$ to be considered as being the identity matrix.

Equation (3) becomes:

$$S_k^E = S_{inc} \times Att \times f_k^E \quad (5)$$

where $f_k^E$ is the scattering function measured by each pixel $20_k$ as a function of energy. From this scattering function, expressed as a function of the energy E, it is possible to establish a scattering function $f_k^\chi$ estimated as a function of the momentum transfer $\chi$, the passage between the vectors $f_k^E$ and $f_k^\chi$ being established by applying the aforementionned matrix $A_k$, with $f_k^E = A_k \cdot f_k^\chi$ In steps 120 and 140, a reference scattering spectrum $S_{k,ref}^E$, obtained for each pixel $20_k$, by placing a reference object $10_{ref}$ made of a known material instead of the object 10, is considered. The scattering properties of the reference object are known. It is then possible to establish a reference scattering function $f_{k,ref}^E$, $f_{k,ref}^\chi$ associated with each pixel $20_k$. Obtaining this reference scattering function will be described in detail hereinafter. Considering that the spectrum $S_{inc}$ of the incident collimated beam $12_c$ does not change between the measurement of the scattering spectrum $S_{k,ref}^E$ of the reference object and the measurement of the scattering spectrum $S_k^E$ of the object to be analyzed, the spectrum of the radiation scattered by each pixel $20_k$ may be expressed as follows:

$$S_{k,ref}^E = S_{inc} \times Att_{ref} \times f_{k,ref}^E \quad (6)$$

where $Att_{ref}$ is an attenuation spectral function of the reference object $10_{ref}$.

It is then possible to form a scattering spectrum denoted $S_k'^E$ normalized by said reference scattering spectrum $S_{k,ref}^E$ and such that:

$$S_k'^E = \frac{S_k^E}{S_{k,ref}^E} = \frac{Att \times f_k^E}{Att_{ref} \times f_{k,ref}^E} \quad (7)$$

This normalization constitutes the step 120. It is possible to determine from this normalized spectrum a scattering function $f_k^\chi$ of each pixel $20_k$, which constitutes the step 140, according to the expression:

Thus, $$f_k^\chi = f_{k,ref}^\chi \times A_k^{-1} \cdot \left[\frac{S_k'^E \times Att_{ref}}{Att}\right] \quad (8)$$

where $f_{k,ref}^\chi$ is the reference scattering function associated with the pixel, expressed as a function of the momentum transfer.

Accordingly, knowing $Att_{ref}$, $f_{k,ref}^\chi$, Att and having measured $S_k^E$, it is possible to estimate $f_k^\chi$ using expression (8).

The aim of step 160 is to obtain a scattering signature representative of each elementary volume of the object from the respective scattering functions $f_k^\chi$ obtained by each pixel $20_k$. In fact, given the angular aperture of the collimator, the same pixel $20_k$ can detect different scattered radiations from respective different elementary volumes.

This spatial dispersion is characterized by an intensity spatial dispersion function $g_k$, each term $g_k(z)$ of which representing an intensity of the radiation scattered by an elementary volume $V_z$ centred on a coordinate z and reaching a pixel $20_k$. This dispersion function $g_k$ is established for each pixel $20_k$. Establishing this dispersion function $g_k$ will be described hereinafter.

An intensity spatial dispersion matrix G can be constituted, each row of which is formed by the various values of the intensity spatial dispersion function $g_k$ associated with a pixel $20_k$ as a function of z. Each term $G(k,z)$ of the matrix G represents the intensity of the signal detected by a pixel $20_k$ and coming from an elementary volume $V_z$ centred at z. In other words, $G(k,z) = g_k(z)$.

The step 160 amounts to taking account of this dispersion matrix in constituting a matrix $F_k$ each row of which represents a scattering function $f_k^\chi$ obtained by a pixel $20_k$. Each term $F_k(k,\chi)$ of this matrix represents a value of the scattering function $f_k^\chi$ measured, at the value $\chi$, by a pixel $20_k$. The dimension of this matrix is $(N_k, N_\chi)$, where $N_k$ is the number of pixels.

The aim is to constitute a matrix $F_z$ of scattering signatures of the object 10 each row of which representing a spectral signature $f_z^\chi$ relating to an elementary volume $V_z$ centred at z. Each term $F_z(z,\chi)$ of this matrix represents a value of the scattering signature (or form factor) at the value $\chi$ of an elementary volume $V_z$. The dimension of this matrix is $(N_a, N_\chi)$, where $N_z$ is the number of elementary volumes $V_z$ concerned.

The intensity spatial dispersion matrix G establishes a connection between the scattering functions of each pixel forming the matrix $F_k$ and the signatures of each elementary volume forming the matrix $F_z$ such that: $F_k = G \cdot F_z$ (9).

It is then a question of obtaining information characterizing the radiation scattered by each elementary volume on the basis of measurements collected at the level of each pixel.

Having determined the intensity spatial dispersion matrix G and having formed from the measurements the matrix of the scattering functions $F_k$, it is possible to obtain an estimate of the matrix of the scattering signatures $F_z$ using an inversion algorithm. The iterative inversion algorithms commonly used include a maximum likelihood expectation maximization (MLEM) type algorithm. According to an algorithm of this kind, the value of each term of the matrix $F_z$ may be estimated using the following expression:

$$\hat{F}_z^n(z,\chi) = \hat{F}_z^{n-1}(z,\chi) \frac{1}{\sum_k G(k,z)} \sum_k \frac{F_k(k,\chi) \cdot G(k,z)}{\sum_z G(k,z) \cdot \hat{F}_z^{n-1}(z,\chi)} \quad (10)$$

the exponent n designating the rank of each iteration. Each iteration then makes it possible to obtain an estimate $\hat{F}_z^n$ of the matrix $F_z$.

The iterations continue until a convergence criterion is reached, which may be a predetermined number of iterations or a low variation between the values estimated during two successive iterations. The use of this algorithm assumes a step of initialization of the matrix $F_z$. For example, this initialization is such that:

$$F_z^{n=0} = \begin{bmatrix} 1 & \cdots & 1 \\ \vdots & \ddots & \vdots \\ 1 & \cdots & 1 \end{bmatrix} \quad (11)$$

At the end of step 160, an estimate of the matrix $F_z$ is obtained, each row of which represents a scattering signature $f_z^\chi$ of a material constituting an elementary volume $V_z$ of the object 10.

During a step 180, the material constituting each elementary volume $V_z$ is identified from the associated scattering signature $f_z^\chi$. For this purpose standard scattering spectral signatures $f_i^\chi$ of various known standard materials $10i$ are provided. These calibration scattering signatures are either established experimentally or obtained from the literature. The proportions $\gamma_z(i)$ of the material $10i$ in the elementary volume $V_z$ may be determined from the expression:

$$(\gamma_z(i=1) \ldots \gamma_z(i=N_i)) = \text{Argmin}(\|f_z^\chi - \Sigma_i \gamma_z(i) f_i^\chi\|^2)$$

where $N_t$ is the number of known calibration materials $10i$.

A vector $\gamma_z$ is obtained each term $\gamma_z(i)$ of which represents a proportion of the material $10i$ in the elementary volume $V_z$.

The method described above assumes the prior establishment of calibration parameters of the measuring system. To be more precise, the method uses for each pixel dispersion functions representing a dispersion of the intensity and/or the scattering angles of scattered radiation detected by said pixel as a function of the positions in the object from which said scattered radiation is emitted. Thus each pixel $20_k$ can be associated to:

an intensity spatial dispersion function $g_k$, mentioned above, representing the intensity of scattering radiation emitted by an elementary volume $V_z$, centred on a coordinate z, and reaching the pixel $20_k$. Knowing the intensity spatial dispersion function of each pixel makes it possible to construct the intensity spatial dispersion matrix G referred to above.

a scattering angle spatial dispersion function denoted $h_k$ representing a distribution of the scattering angles $\theta$ of the scattered radiation $14_\theta$ detected by the pixel $20_k$.

a scattering intensities angular dispersion function denoted $j_k$ representing a distribution of the intensity of the scattering radiation detected by the pixel as a function of the scattering angle. Knowing this dispersion function makes it possible to determine the angular response matrix $A_k$ described above of the pixel $20_k$ and/or the mean scattering angle $\theta_k$ of said pixel. Thus knowing this angular dispersion function makes it possible to generate a change of variable between the energy E and the momentum transfer $\chi$ and vice versa using the angular response matrix.

One object of the invention is to establish at least one of these dispersion functions, in particular experimentally, the inventors considering that this kind of determination is more reliable than modelling based on calculation codes.

Obtaining the Intensity Spatial Dispersion Functions $g_k$

The passage between the scattering functions $f_k^\chi$ measured by a pixel and the scattering signatures $f_z^\chi$ of the radiation emitted by an elementary volume $V_z$ requires the use of intensity spatial dispersion functions $g_k$ associated with each pixel $20_k$ from which it is possible to establish the intensity spatial dispersion matrix G described above with reference to the step 160. These intensity spatial dispersion functions $g_k$ can be obtained experimentally, using a calibration object $10_c$ consisting of a known material taking the form of a thin plate that can be moved successively along the propagation axis $12_z$ of the incident collimated beam $12_c$. By thin plate is meant a width in the order of that of an elementary volume, i.e. in the order of the spatial resolution that it is required to obtain.

Figure 3A:
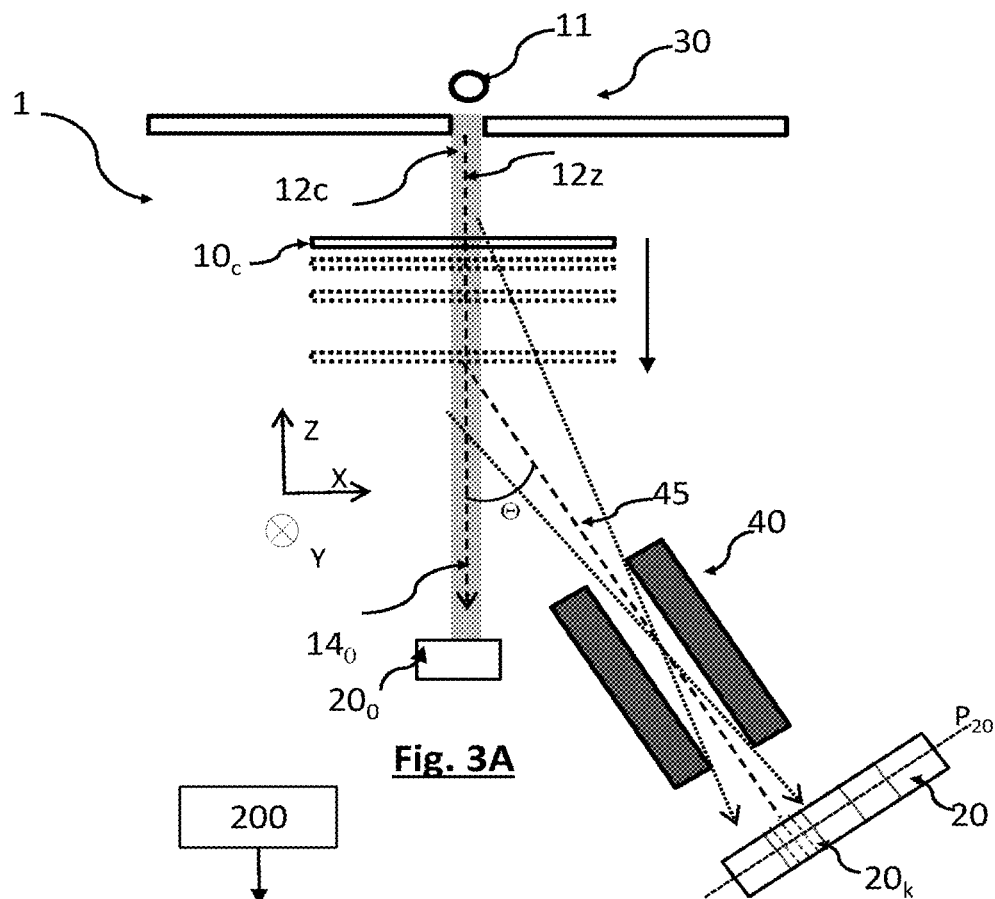
FIG. 3A represents a device making it possible to obtain the dispersion function described in this application.
Figure 3B:
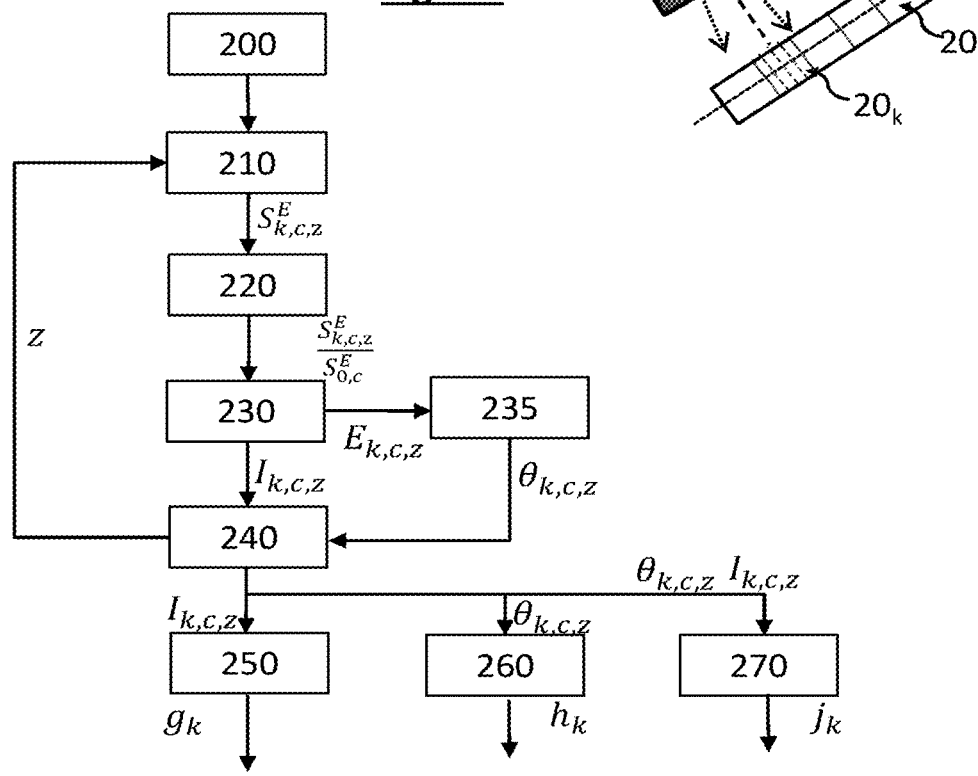
FIG. 3B illustrates the main steps of a method making it possible to obtain such functions.

FIG. 3A represents a device making it possible to obtain spatial dispersion functions of each pixel $20_k$ in connection with the main steps of the method illustrated by FIG. 3B. The calibration object $10_c$ is moved in translation along the propagation axis $12_z$ so as to occupy successively the various elementary volumes $V_z$ of an analyzed object. In each position z of the calibration object $10_c$, the latter is irradiated by the irradiation source 11 and each pixel $20_k$ acquires a calibration spectrum $S_{k,c,z}^E$ of the scattered radiation when the calibration object occupies a position z.

The calibration object $10_c$ is chosen so that its scattering signature, i.e. the momentum transfer spectrum of the scattered radiation during the irradiation of this object, features characteristic peaks. There may for example be chosen aluminium, 3 mm thick, having a characteristic peak at 2.0248 Å. This corresponds to a momentum transfer $\chi = 2.469$ nm$^{-1}$. The thickness of the calibration object must be consistent with the required spatial resolution. It may be between 1 mm and 1 cm inclusive if a spatial resolution better than 1 cm is required, for example.

Figure 3C:
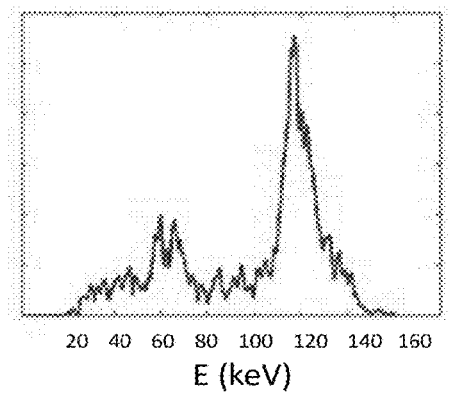
FIGS. 3C and 3D show one example of a calibration spectrum featuring a characteristic diffraction peak, termed the calibration peak, the intensity and/or the energy of which can be measured to constitute a spatial or angular dispersion function.
Figure 3D:
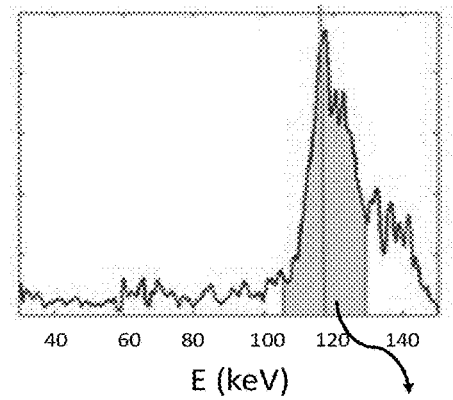

Let us consider for example a pixel $20_k$ configured essentially to receive scattering radiation emitted at an angle θ of 2.5°. FIG. 3C represents a spectrum $S_{k,c,z}^E$ of the scattered radiation acquired by this pixel. The spectrum can be normalized by a transmission spectrum $S_{0,c}^E$ measured by the auxiliary detector $20_0$ in transmission mode in order to obtain a normalized spectrum represented in FIG. 3D. The transmission spectrum $S_{0,c}^E$ corresponds to a spectrum of radiation that has passed through the calibration object $10_c$ parallel to the propagation axis $12_z$ without having interacted with the calibration object $10_c$. A so-called calibration peak is seen, centred on an energy of 120 keV, which conforms to the energy E obtained from equation (2) taking χ=2.469 nm$^{-1}$ and θ=2.5°. The calibration peak extends on either side of 120 keV because of the energy resolution of the detector and the angular dispersion associated with the pixel $20_k$. Its integral $I_{k,c,z}$ represented in FIG. 3D can easily be obtained using a spectrum processing algorithm, as usual in the spectrometry field. This integral represents a quantity of radiation detected by the pixel $20_k$ in the calibration peak when the calibration object is placed at a position z. At each position z of the calibration object $10_c$ the integral $l_{k,c,z}$ of the calibration peak is therefore determined on the basis of the calibration spectrum $S_{k,c,z}^E$, preferably normalized by the transmission spectrum $S_{0,c}^E$. The intensity spatial dispersion function $g_k$ associated with each pixel $20_k$ then includes, for all the positions z, the integral $l_{k,c,z}$ of the calibration peak. In other words: $g_k(z)=I_{k,c,z}$ (13)

Intensity values $I_{k,c,z}$ are then available representing a quantity of photons detected by a pixel $20_k$ in a representative peak of the calibration object $10c$ when the latter occupies a position z in the object.

Figure 3E:
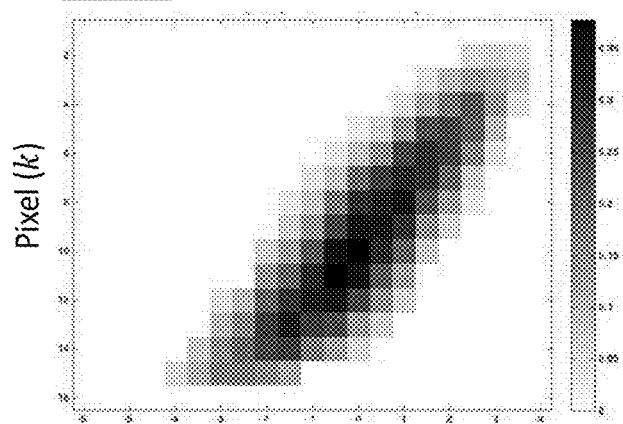
FIG. 3E represents so-called spatial dispersion functions respectively associated with various pixels.

It is then possible to establish the intensity spatial dispersion matrix G as represented in FIG. 3E in which each term $G(k,z)=g_k(z)=I_{k,c,z}$. This matrix represents the intensity of scattered radiation detected by a pixel $20_k$ coming from an elementary volume $V_z$ of the object centred at z. It is of dimension $(N_k,N_z)$. Each row k of this matrix represents an intensity spatial dispersion function $g_k$ of a pixel $20_k$ associated with said row. The intensity values $I_{k,c,z}$ are expressed on a grey scale.

The determination of the spatial dispersion matrix G therefore comprises the following steps:
  placing the calibration object $10_c$ made of a known material, so called calibration material, at a position z in the observation field of the detector 20 (step 200);
  at said position z, measurement of the calibration spectrum $S_{k,c,z}^E$ by the pixels $20_k$ of the detector 20 (step 210);
  normalization of each calibration spectrum $S_{k,c,z}^E$ by a transmission spectrum $S_{c,0}^E$ measured through the calibration object by the auxiliary detector $20_0$ (step 220), such normalization being optional but preferable;
  in each calibration spectrum thus normalized, determination of the intensity $I_{k,c,z}$ of a calibration peak representative of the material constituting the calibration object (step 230);
  reiterating steps 210 to 230 with the calibration object moved to different successive positions z in the observation field of the second collimator (step 240);
  using the intensities $I_{k,c,z}$, obtaining the spatial dispersion function $g_{k,z}$ associated with each pixel and obtaining the spatial dispersion matrix G (step 250).

At some positions z of the calibration object $10_c$, the calibration spectrum $S_{k,c,z}^E$ measured by a pixel $20_k$ may not include an identifiable calibration peak. In this case, this calibration spectrum is not taken into account to determine the dispersion function associated with the pixel.

Obtaining the Scattering Angles Spatial Dispersion Function $h_k$

Refer again to FIG. 3B. The determination of a scattering angles spatial dispersion function $h_k$ associated with a pixel $20_k$ is carried out through the steps 200, 210, 220, and 230, the steps 210 to 230 being executed for different positions z in the observation field of the second collimator 40.

On each calibration spectrum $S_{k,c,z}^E$ acquired by a pixel $20_k$, and preferably normalized by the transmission spectrum $S_{0,c}^E$ the energy $E_{k,c,z}$ is determined corresponding to a representative calibration peak of a material constituting the calibration peak. This material being known, the momentum transfer corresponding to the energy of the calibration peak is also known, for example χ=2.469 nm$^{-1}$ for aluminium. The step 230 determines the energy $E_{k,c,z}$ of the calibration peak.

The scattering angle $\theta_{k,c,z}$ associated with this peak can be obtained using expression (2), knowing the energy $E_{k,c,z}$. Accordingly, with each position z for which the calibration spectrum $S_{k,c,z}^E$ has an identifiable calibration peak, there may be associated a scattering angle $\theta_{k,c,z}$ of the scattering radiations detected by the pixel $20_k$. The step 235 determines this scattering angle. If the calibration material occupies certain positions z, a pixel may collect no scattering radiation. In this case, the calibration spectrum $S_{k,c,z}^E$ does not cause any meaningful peak to appear and there is no therefore scattering angle associated with the pixel at this position.

Figure 3F:
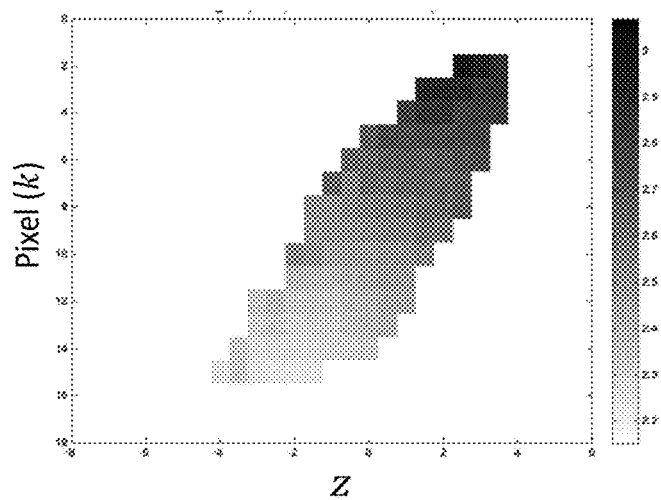
FIG. 3F represents so-called angular dispersion functions respectively associated with the pixels of FIG. 3E.

FIG. 3F represents the various scattering angles $\theta_{k,c,z}$ associated with each pixel $20_k$ as a function of the position z of the calibration object along the propagation axis $12_z$. In this figure, the abscissa axis represents the position z and the ordinate axis is the reference of the pixel $20_k$, knowing that here it is a question of virtual pixels spaced by 150 μm. The values of the scattering angles $\theta_{k,c,z}$ are expressed according to the grey scale.

The distribution of the scattering angles $\theta_{k,c,z}$ of the scattered radiation detected by a pixel $20_k$ as a function of the position z constitutes a spatial dispersion function of the scattering angles $h_k$ of said pixel such that $h_k(z)=\theta_{k,c,z}$, where $\theta_{k,c,z}$ is one of the scattering angles determined at a position z of the calibration object. This function is determined in the step 260. Each row k in FIG. 3F represents a spatial dispersion function of scattering angles $h_k$ of a pixel $20_k$. This dispersion function is discrete and is defined only for the coordinates z for which a scattering angle $\theta_{k,c,z}$ has been determined for said pixel $20_k$, i.e. a scattering angle for which the calibration spectrum $S_{k,c,z}^E$ has a useable calibration peak.

Moreover, for each pixel $20_k$/position z pair there may be established an intensity $I_{k,c,z}$ of a calibration peak, as described with reference to the determination of the intensity spatial dispersion function $g_k$.

A mean scattering angle $\theta_k$ for a pixel $20_k$ can be determined by producing a mean of each scattering angle $\theta_{k,c,z}$ corresponding to a position z weighted by the intensity $I_{k,c,z}$ of the calibration peak corresponding to that same position.

In other words, $$\theta_k = \sum_z \frac{\theta_{k,c,z} \times I_{k,c,z}}{I_{k,c,z}} = \sum_z \frac{h_k(z) \times I_{k,c,z}}{I_{k,c,z}} \quad (17)$$

FIG. 4A represents the mean dispersion angles $\theta_k$ obtained for various pixels $20_k$. FIG. 4B represents the effect of a change of variable using said mean dispersion angle. There is represented in this figure a cumulative energy spectrum $S^E$ obtained by summing the spectra $S_k^E$ acquired by 16 virtual pixels $20_1 \ldots 20_{16}$ when the object consists of aluminium. Moreover, each spectrum acquired by each virtual pixel $20_k$ has been recalibrated by effecting a change of variable between the energy E and the momentum transfer according to the equation:

$$\chi = \frac{E\sin\left(\frac{\theta_k}{2}\right)}{hc}, \tag{18}$$

$\theta_k$ representing the mean scattering angle associated with the pixel $20_k$. The spectra recalibrated in this way, denoted $S_k^\chi$ because they depend on the momentum transfer, have been summed so as to constitute a cumulative spectrum $S^\chi$ of the momentum transfer. This spectrum is represented in FIG. 4B. The spectrum $S^\chi$ obtained after summation of the recalibrated spectra makes it possible to identify better a characteristic peak of aluminium at $\chi=2.469$ nm$^{-1}$.

Obtaining Intensity Angular Dispersion Functions $j_k$

For each pixel $20_k$ it is possible to establish both the intensity $I_{k,cz}$ and the scattering angle $\theta_{k,cz}$ of a calibration peak obtained over a calibration spectrum $S_{k,cz}^E$ when the calibration object $10_c$ is placed at each position z. An intensity angular dispersion function, $j_k$, can then be obtained for said pixel. It is then expressed in the form $j_k(\theta)=I_{k,cz}$ when $\theta=\theta_{k,cz}$. Referring to FIG. 3B, this function is determined in the step 270. FIG. 5A shows intensity angular dispersion functions associated with various pixels. Each intensity angular dispersion function associated with a pixel $20_k$ is discrete and is defined only for the scattering angles $\theta_{k,cz}$ for which the calibration spectrum has a useable calibration peak. The grey scale determines the pixels whose intensity angular dispersion functions are represented in this figure.

Each intensity angular dispersion function $j_k$ can be interpolated in order to obtain a continuous distribution between the various angles $\theta_{k,cz}$. A so-called interpolated intensity angular dispersion function $j_k^i$ is then obtained, the exponent i designating the fact that the angular dispersion function is interpolated. FIG. 5B represents the interpolated intensity angular dispersion functions obtained for various pixels from the intensity angular dispersion functions plotted in FIG. 5A. The grey scale of FIG. 5B is the same as that used for FIG. 5A.

For each pixel $20_k$, the interpolated intensity angular dispersion function $j_k^i$ associated with a pixel $20_k$ makes it possible to establish the angular response matrix $A_k$ associated with said pixel mentioned above. Each row (or column) of said angular response matrix $A_k$ is associated with an energy E and represents a probability distribution of the momentum transfer $\chi$ when said pixel detects radiation with said energy E.

FIG. 5C represents an angular response matrix of this kind in which each term $$A_k(E, \chi) = j_k(\theta) \text{ if } E = \frac{hc\chi}{\sin\left(\frac{\theta}{2}\right)}.$$

Using small pixels physical or virtual pixels makes it possible to limit the observation field of each pixel. Because of this, in the present example the angular dispersion matrix $A_k$ can be considered as being the diagonal matrix, with $A_k(E,\chi)=1$ if $$E = \frac{hc\chi}{\sin\left(\frac{\theta_k}{2}\right)}$$

this diagonal matrix represented in FIG. 5D, $\theta_k$ being defined by expression (17).

Thus the determination of an intensity angular dispersion function, whether discrete or interpolated, makes it possible to establish an angular dispersion matrix for each pixel of the detector.

Obtaining the Scattering Function $f_{k,ref}^\chi$ of the Reference Material for Each Pixel $20_k$.

The step 160 requires a knowledge of a scattering function $f_{k,ref}^\chi$ of each pixel $20_k$ when it detects scattering radiation coming from the reference material $10_{ref}$. In the presence of such a material, occupying all the elementary volumes $V_z$ in the observation field of the second collimator 40, the scattering signature $f_{z,ref}^\chi$ of each elementary volume $V_z$ corresponds to a scattering signature $f_{ref}^\chi$ of the reference material, which is known and common to all the elementary volumes. The scattering function $f_{k,ref}^\chi$ of each pixel is obtained from expression (9), constituting a matrix $F_{Z,ref}$ each row of which corresponds to the scattering signature $f_{ref}^\chi$ of the reference material. There is obtained a matrix $F_{k,ref}=G.F_{Z,ref}$(16), each row of the matrix $F_{k,ref}$ representing the scattering function $f_{k,ref}^\chi$ associated with each pixel $20_k$ of the reference object $10_{ref}$.

Obtaining Attenuation Spectral Functions

The method described above preferably assumes the use of attenuation spectral functions Att and Att$_{ref}$ respectively representing the attenuation of the incident collimated beam $12_c$ by the object 10 and by the reference object $10_{ref}$. These functions are respectively obtained using the auxiliary detector $20_0$ in transmission mode, the latter measuring:

an energy spectrum $S_{inc}$ of the incident collimated beam $12_c$, that spectrum being obtained with no object placed between the detector $20_0$ and the first collimator 30.

an energy spectrum $S_0^E$ or $S_{0,ref}^E$ of the radiation $14_0$ transmitted along the propagation axis $12_z$ by the object 10 or the reference object $10_{ref}$. This transmitted radiation has not interacted with the object (or with the reference object).

Having acquired these spectra, it is possible to define an attenuation spectral function by a comparison of those spectra, generally in the form of a ratio. Thus the attenuation Att of the object 10 is obtained by a ratio between $S_{inc}$ and $S_0^E$ and the attenuation Att$_{ref}$ of the reference object is obtained by a ratio between $S_{inc}$ and $S_{0,ref}^E$. This corresponds to the following equations:

$$Att = \frac{S_{inc}}{S_0^E}; \tag{20}$$

$$Att_{ref} = \frac{S_{inc}}{S_{0,ref}^E} \tag{21}$$

Experimental Trial

An experimental trial was carried out using a test object $10_{test}$ consisting of a copper plate $10_{test-1}$ 1 cm thick and an aluminium plate $10_{test-2}$ 1 cm thick, these two plates being spaced by 2 cm. Here the collimation angle $\Theta$ is equal to 5°. The experimental set up is represented in FIG. 6A.

The reference measurements $f_{k,ref}^E$ and $Att_{ref}$ making it possible to obtain scattering functions $f_k^E$ of each pixel (cf. step 140) are effected using a block of PMMA 10 cm thick.

The PMMA block was placed first, before determining a transmission spectrum $S_{0,ref}^E$, using the auxiliary detector $20_0$. That auxiliary detector also makes it possible to measure a spectrum $S_{inc}$ of the incident collimated beam $12_c$ with no object disposed between the auxiliary detector $20_0$ and the first collimator 30. A spectral function $Att_{ref}$ was determined in this way for the attenuation of the reference material on the basis of a ratio between $S_{0,ref}^E$ and $S_{inc}$ according to equation (21).

There was also determined the spectrum $S_{k,ref}^E$ of the scattering radiation of the reference material, in this instance PMMA, for various virtual pixels $20_k$. FIG. 6B represents these various spectra. In that figure, the abscissa axis represents the energy and the ordinate axis represents the reference of each virtual pixel, the grey scale representing the intensity. Each line of this figure represents the spectrum acquired by each pixel, the intensity being indicated by the grey scale.

The attenuation spectral function Att of the test object $10_{test}$ was then determined by carrying out a measurement of a spectrum by the auxiliary detector $20_0$ with and without the test object so as to acquire the respective spectra $S_0^E$ and $S_{inc}$, the ratio of which makes it possible to establish this attenuation spectral function Att according to expression (20).

There were then acquired the scattering spectra $S_k^E$ of the test object by various virtual pixels $20_k$, those spectra being represented in FIG. 6C. In that figure, the abscissa axis represents the energy and the ordinate axis represents the reference of each virtual pixel, the intensity being indicated by the grey scale.

Each scattering spectrum was then normalized according to equation (7) using the spectra $S_{k,ref}^E$ so as to obtain for each pixel g a normalized spectrum $S'_k^E$.

From each normalized spectrum $S'_k^E$ there were obtained the spectral signatures $f_k^\chi$ of each pixel $20_k$ expressed as a function of the momentum transfer $\chi$ (cf. equation 8) using a scattering function $f_{k,ref}^\chi$ of the reference material $10_{ref}$ established using equation 16. FIGS. 6D and 6E respectively represent the scattering signatures $f_k^E$ and $f_k^\chi$ respectively expressed as a function of the energy and the momentum transfer. The intensity is indicated by the grey scale.

Knowing the spatial dispersion matrix G, the scattering signature $f_z^\chi$ was obtained of various elementary volumes distributed in the object along the propagation axis $12_z$ by applying equations (9) and (10). These scattering signatures are given in FIG. 6F, the coordinate z=0 designating the centre of the test object. Specific signatures of aluminium and copper are indeed seen.

FIG. 6G illustrates the various materials finally determined as a function of the coordinate z. Copper and aluminium are correctly identified. The air gap between the two materials was not identified, which explains that the gap between the aluminium and the copper is considered as occupied either by aluminium or by copper. The presence of water at one end of the object is the result of an edge effect.

The invention could be used in nondestructive testing type applications or medical diagnostic aid type applications, using a collimator including only one channel, as described in the above detailed description, or a collimator including a plurality of channels.

Moreover, although described in connection with a second collimator 40 having a single channel 42, the method of establishing dispersion functions, whether that means an angular dispersion function or a spatial dispersion function, can be applied to other types of collimation, for example collimators having a plurality of channels, for example channels disposed parallel to one another, or coded mask type collimation, by virtue of which the same pixel sees the object via different channels.

The invention claimed is:

1. A method of calibrating a device for analyzing an object, said analysis device including:
    a source of irradiation adapted to irradiate said object, configured to emit ionizing electromagnetic radiation propagating toward the object along a propagation axis;
    a detector including at least one pixel and adapted to detect radiation scattered by the object irradiated in this way and to acquire an energy spectrum thereof, said scattered radiation propagating in a direction at an acute scattering angle relative to said propagation axis;
    the calibration method including the following steps:
    a) irradiating a calibration object by the irradiation source so that at least one pixel of the detector detects radiation scattered by the calibration object thus irradiated and acquires an energy spectrum thereof;
    b) moving the calibration object to successive different positions along said propagation axis, and at each position of the object, acquisition, by said pixel, of a calibration spectrum, of the radiation scattered by the calibration object, each calibration spectrum being associated with a position of the calibration object;
    c) in each calibration spectrum acquired during the step b), identification of a characteristic calibration peak of the calibration object;
    d) from each characteristic calibration peak identified in step c), determining a parameter of the calibration peak;
    e) obtaining a dispersion function associated with the pixel from parameters determined during the step d) at the various positions of said calibration object, said dispersion function representing a dispersion of the intensity and/or the scattering angle of scattered radiation detected by said pixel at the various positions of the calibration object.

2. The Method according to claim 1, in which:
    step d) includes determining an intensity of the each calibration peak identified in each calibration spectrum; and
    step e) includes determining an intensity spatial dispersion function from the intensities of the calibration peak, determined at each position of the calibration object, said dispersion function representing a quantity of scattered radiation detected by the pixel as a function of the position of the calibration object.

3. The Method according to claim 1 in which:
    step d) includes determining an energy of the calibration peak identified in each calibration spectrum; and
    step e) includes:
    calculating a scattering angle from the energy determined in each calibration spectrum;
    determining a spatial dispersion function of the scattering angles from the scattering angles obtained at each position of the calibration object, said dispersion function representing the scattering angles of the scattered radiation detected by said pixel as a function of the position of the calibration object.

4. The Method according to claim 3, including a step f) of determining a mean scattering angle for said pixel.

5. The Method according to claim 1, in which:
step d) includes determining an intensity and the energy of said calibration peak identified in each calibration spectrum; and
step e) includes:
calculating a scattering angle from said energy determined at each calibration peak, said scattering angle being associated with said intensity of said calibration peak; and
determining an intensity angular dispersion function representing a distribution of the intensity of the scattering radiation detected by the pixel as a function of the scattering angle of that radiation.

6. The Method according to claim 5, including a step f) of interpolating the intensity angular dispersion function between the various scattering angles obtained in the step e) at each position of the calibration object, so as to obtain an interpolated intensity angular dispersion function.

7. The Method according to claim 6 including a step g) of determining an angular response matrix associated with said pixel from said interpolated intensity angular dispersion function, wherein each row or column of said matrix is associated with an energy and representing a probability distribution of the momentum transfer when the pixel detects scattering radiation with said energy.

8. The Method according to claim 1, in which the detector includes a plurality of pixels, the method including determining a dispersion function for each pixel.

9. The Method according to claim 1, in which the pixels are virtual pixels obtained by sub-pixelization of physical pixels of the detector.

10. An information storage medium readable by a processor including instructions for the execution of the steps c) to e) of the method according to claim 1 using acquisition spectra acquired by a pixel of a detector, the spectrum being acquired according to the steps a) and b) of the method according to claim 1, those instructions being executable by the processor.

* * * * *